(12) United States Patent
Skjervold et al.

(10) Patent No.: US 7,290,925 B1
(45) Date of Patent: Nov. 6, 2007

(54) FULL HISTORY TIME-TEMPERATURE INDICATOR SYSTEM

(75) Inventors: Per Olav Skjervold, Ås (NO); Brit Salbu, Oslo (NO); Petter Hieronymus Heyerdahl, Ås (NO); Helge Lien, Levanger (NO)

(73) Assignee: TimeTemp AS, Ås (NO)

( * ) Notice: Subject to any disclaimer, the term of this patent is extended or adjusted under 35 U.S.C. 154(b) by 0 days.

(21) Appl. No.: 10/110,498

(22) PCT Filed: Oct. 9, 2000

(86) PCT No.: PCT/IB00/01443

§ 371 (c)(1),
(2), (4) Date: Oct. 8, 2002

(87) PCT Pub. No.: WO01/27608

PCT Pub. Date: Apr. 19, 2001

(30) Foreign Application Priority Data

Oct. 11, 1999 (DK) ................. 1999 01450

(51) Int. Cl.
*G01K 3/04* (2006.01)
(52) U.S. Cl. .............. 374/106; 374/162; 374/159; 116/216
(58) Field of Classification Search ........ 374/102, 374/106, 159, 208, 161, 162; 116/200, 206, 116/216
See application file for complete search history.

(56) References Cited

U.S. PATENT DOCUMENTS

| | | | | |
|---|---|---|---|---|
| 3,055,759 A | * | 9/1962 | Busby et al. | 116/207 |
| 3,895,523 A | * | 7/1975 | Nollen | 73/356 |
| 3,962,920 A | * | 6/1976 | Manske | 374/102 |
| 3,967,579 A | * | 7/1976 | Seiter | 73/358 |
| 3,999,946 A | | 12/1976 | Patel et al. | 23/253 TP |
| 4,042,336 A | * | 8/1977 | Larsson | 23/253 TP |
| 4,137,049 A | * | 1/1979 | Couch et al. | 422/56 |
| 4,253,304 A | * | 3/1981 | Lamb et al. | 60/527 |
| 4,313,761 A | * | 2/1982 | Joyce, III et al. | 106/18.19 |
| 4,457,252 A | * | 7/1984 | Manske | 116/216 |
| 4,457,253 A | * | 7/1984 | Manske | 116/216 |
| 4,533,640 A | | 8/1985 | Shafer | 436/2 |
| 4,601,588 A | * | 7/1986 | Takahara et al. | 374/106 |
| 4,643,122 A | * | 2/1987 | Seybold | 116/206 |
| 4,643,588 A | * | 2/1987 | Postle et al. | 374/160 |
| 4,675,161 A | * | 6/1987 | Hashimoto et al. | 422/56 |
| 4,729,671 A | * | 3/1988 | Asano et al. | 374/160 |

(Continued)

FOREIGN PATENT DOCUMENTS

EP 0484578 A1 5/1992

(Continued)

*Primary Examiner*—Gail Verbitsky
(74) *Attorney, Agent, or Firm*—Roberts, Mlotkowski & Hobbes P.C.

(57) ABSTRACT

A full-history time-temperature indicator system which is capable of exhibiting a time-temperature dependent and visually detectable chemical reaction, useful for monitoring the time and temperature exposure of food products. The system comprises an immobilized reactant, such as $Fe^{3+}$, and a mobile reactant, such as $Fe(CN)_6^{4-}$, initially contained in separate compartments, and separated by a sealing. The system is activated by removing a sealing between the compartments whereby the mobile reactant in a time-temperature dependent manner is brought into contact with the immobilized reactant resulting in a visually detectable reaction signal.

38 Claims, 2 Drawing Sheets

U.S. PATENT DOCUMENTS

| | | | | |
|---|---|---|---|---|
| 4,743,557 | A | * | 5/1988 | Tiru et al. ...................... 436/2 |
| 4,753,188 | A | * | 6/1988 | Schmoegner ............... 116/217 |
| 5,045,283 | A | | 9/1991 | Patel ........................... 422/56 |
| 5,053,339 | A | | 10/1991 | Patel ............................. 436/2 |
| 5,057,434 | A | | 10/1991 | Prusik et al. ................... 436/2 |
| 5,110,215 | A | * | 5/1992 | Labes .......................... 374/106 |
| 5,158,364 | A | * | 10/1992 | Labes .......................... 374/106 |
| 5,182,212 | A | | 1/1993 | Jalinski ......................... 436/2 |
| 5,215,378 | A | * | 6/1993 | Manske ...................... 374/105 |
| 5,637,475 | A | * | 6/1997 | Narayan ....................... 435/31 |
| 5,667,303 | A | * | 9/1997 | Arens et al. ................. 374/102 |
| 5,695,284 | A | * | 12/1997 | Waters ........................ 374/162 |
| 5,709,472 | A | * | 1/1998 | Prusik et al. ................ 374/106 |
| 6,029,601 | A | * | 2/2000 | Suya .......................... 116/217 |
| 6,289,794 | B1 | * | 9/2001 | Carmon ....................... 99/342 |
| 6,378,454 | B1 | * | 4/2002 | Massi .......................... 116/219 |
| 6,452,873 | B1 | * | 9/2002 | Holt et al. ................... 368/327 |
| 2003/0214997 | A1 | * | 11/2003 | Diekmann et al. .......... 374/102 |

FOREIGN PATENT DOCUMENTS

| | | | |
|---|---|---|---|
| EP | 0735368 | A1 | 10/1996 |
| GB | 2151784 | A | 7/1985 |
| GB | 2332517 | A | 6/1999 |
| WO | WO91/09287 | A1 | 6/1991 |
| WO | WO92/08113 | A1 | 5/1992 |
| WO | WO93/22638 | A1 | 11/1993 |
| WO | WO96/28714 | A1 | 9/1996 |
| WO | WO9628714 | A1 * | 9/1996 |
| WO | WO97/28228 | A1 | 8/1997 |

* cited by examiner

FULL HISTORY TIME-TEMPERATURE INDICATOR SYSTEM

This application is a 35 U.S.C. § 371 of International Application No. PCT/IB00/01443 filed Oct. 9, 2000, which claims priority from Denmark patent application PA 1999 01450, filed Oct. 11, 1999.

FIELD OF INVENTION

The invention pertains to the provision of a time-temperature indicator system useful for monitoring the environmental exposure of products that undergo progressive quality changes in response to such exposures. In particular there is provided a full-history time-temperature indicator system for the cumulative monitoring of the time and temperature exposure of especially perishable products.

TECHNICAL BACKGROUND AND PRIOR ART

The quality of food products and other perishables are highly dependent on storage conditions such as the temperature and the storage time from production or packing until it finally reaches the end consumer. The deterioration processes are faster when the temperature is raising due to increasing biochemical reaction rates, and therefore the quality of perishable goods declines more rapidly at high temperatures than at low temperatures.

Examples of perishable goods which need to be stored under conditions such that a particular temperature limit is not exceeded or at least not exceeded for longer than a predetermined period of time, include fresh food products, chilled food products and food products that have been pre-cooked or processed by freezing, irradiation, partial cooking, freeze drying or steaming. If such products are not stored under appropriate temperature conditions then there is a danger of propagation of microorganisms which are injurious to human health or of spoilage organisms. Further examples of products which may need to be stored under appropriate temperature conditions are certain pharmaceuticals which would otherwise deteriorate.

Currently only date marking is applied for the insurance of storage quality. By date marking only, no information is given to the consumer or others about the storage conditions to which the product has been exposed, hence the purchasers of susceptible products are not able to determine whether the product has been stored under appropriate temperature conditions during the time of storage. Relying on date marking as a sole quality criterion presupposes that the perishable product has been stored under appropriate conditions throughout the entire storage period. The end consumer will e.g. not be able to determine if a frozen product has been thawn during transportation and subsequently frozen before being put on sale. To be on the safe side, producers of perishable goods often use date marking with a wide safety margin, hence products which are actually still suitable for consumption or use are often discarded.

Therefore, there is a continuing interest in the monitoring of the time and temperature to which storage sensitive products have been exposed in e.g. food distribution chains from factory to consumer.

By supplying a perishable product with a time-temperature indicator which follows the individual product from packing to sale, the producer, the grosser, the retailer and the consumer will have a better product control than they have currently. By the use of a time-temperature indicator, the true shelf life of the products can be monitored, which means that discarding can be retarded until the applied time-temperature indicator has detected that storage conditions have not been appropriate and/or that the recommended storage time has been exceeded.

Time-temperature indicators may be classified as either partial history or full history indicators depending on their response mechanism. Partial history indicators will not respond unless a threshold temperature has been exceeded, while full history indicators respond independently of a temperature threshold and provides a cumulative response to the time and storage conditions to which the time-temperature indicator (and hence the product) has been exposed.

Thus, EP 505 449 B1 discloses an example of a partial history time-temperature indicator comprising a fusible material such as polycaprolactone triol, polyethylene glycol $C_{1-4}$ alkyl ether and polyvinyl alcohol, which flows when a given threshold temperature is exceeded and re-solidifies when exposed to temperatures below the same temperature. The fusible material flows in a substrate and an indicator system produces a physically detectable change in the substrate when the fusible material flows therein.

Partial history time-temperature indicators such as the above described, do not provide a direct measure of time-temperature history. This is most important, since the degradation of perishables depend on the time exposure to particular temperatures. For example, food exposed for a period of time to one temperature may degrade to the same extent if exposed to a shorter period of time at a higher temperature. Hence there are several advantages in using full history time-temperature indicators.

However, there are a number of general requirements that a full history time-temperature indicator should fulfill. These include that the indicator gives a continuous and cumulative response to time and temperature, and that the response to time and temperature is generated gradually and is a function of both time and temperature. The response to time and temperature should be irreversible to prevent the time-temperature indicator from being reset. Preferably it should also be capable of indicating the time-temperature history within a wide temperature range.

The indicator should furthermore in conjunction with a perishable product, show the real condition of this product, and e.g. reflect the storage conditions to which the product has been exposed and be able to show if a frozen product has been defrosted for a period of time. It should also be conveniently activated so that pre-usage storage of the indicator is not a problem, and the response to time and temperature should be given in a visually and easily interpretable manner. Finally, and importantly, it should be non-toxic and not pose any thread to human health.

According to present invention there is now provided a full history time-temperature indicator which fulfill all of the above mentioned requirements. The response given by the time-temperature indicator according to the invention is easily read by the human eye, and in conjunction with a product it gives a measure of the storage conditions to which the product has been exposed by giving a cumulative response to time-temperature exposure.

SUMMARY OF THE INVENTION

Accordingly, the invention relates in a first aspect to a full-history time-temperature indicator system which is capable of exhibiting a time-temperature dependent and visually detectable chemical reaction. The system comprises at least one immobilized and at least one mobile reactant, wherein the reactants are contained in separate adjacent compartments, and the reactants initially are separated by a sealing to prevent contact between the reactants. The rate of mobility of the mobile reactant is time-temperature dependent and the system is activatable by removing the sealing between the compartments whereby the mobile reactant in a time-temperature dependent manner is brought into contact with the immobilized reactant, resulting in a visually detectable reaction signal that indicates the time-temperature history.

In a further aspect there is also provided a method for monitoring the time-temperature history of a product, comprising defining a typical time-temperature history for said product which results in a desired or an undesired change of the product. The method comprises the construction of a system as defined above which provides a visually detectable reaction signal indicating that the desired or the undesired change of the product is imminent, associating the product with the constructed system, activating the system and following the visually detectable reaction signal during storage of the product.

In a still further aspect, the invention pertains to a method for producing a full-history time-temperature indicator system. The method comprises the selection of at least two reactants which, when brought into contact, provides a visually detectable chemical reaction, immobilizing one of the reactants in a medium, which permits the other of the reactants to become mobile, enclosing the mobile reactant and the medium containing the immobilized reactant in adjacent compartments separated by a breakable sealing.

DETAILED DISCLOSURE OF THE INVENTION

Figure 1:
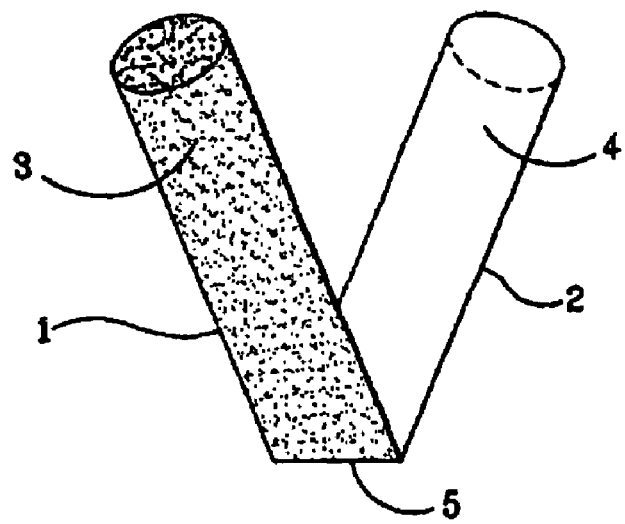
FIG. 1 is a conceptual representation of one exemplary embodiment of the system of the invention before activation.

Thus, in one aspect the present system contemplates a full-history time-temperature indicator system which is capable of exhibiting a time-temperature dependent and visually detectable chemical reaction.

The system comprises, as it is mentioned above, at least one immobilized and at least one mobile reactant, wherein the reactants are contained in separate adjacent compartments. The reactants are initially separated by a sealing to prevent contact between the reactants. The rate of mobility of the mobile reactant is time-temperature dependent and the system can be activated by removing or breaking the sealing between the compartments whereby the mobile reactant in a time-temperature dependent manner is brought into contact with the immobilized reactant, resulting in a visually detectable reaction signal that indicates the time-temperature history.

In one useful embodiment of the system according to the invention, the reactants are metal compounds from the transition metal group (IB-VIIIB), metal compounds from the groups IIIA, IVA and VA in the periodic table, such as ions from the group consisting of Fe, Mn and Al or metals from the rare-earth elements (Lanthanoids).

The reactants may also be a metal reacting or metal binding compound.

The chemical reaction between the reactants can result in a redox process and/or the formation of e.g. a complex, a chelate and a compound with low solubility (precipitate).

In a presently preferred embodiment of the invention as described herein, the mobile reactant is $Fe(CN)_6^{4-}$, however also the use of $Fe^{3+}$ as mobile reactant is also contemplated. The ion $Fe(CN)_6^{4-}$ can e.g. be derived from $K_4Fe(CN)_6$ and the ion $Fe^{3+}$ can e.g. be achieved from $FeCl_3$.

When using the presently preferred mobile chemical reactant, $Fe(CN)_6^{4-}$, in the system, a strongly blue coloured compound is formed when $Fe^{3+}$ is the immobilized reactant. The blue coloured compound has low solubility and is formed by the reaction:

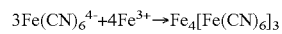
$$3Fe(CN)_6^{4-} + 4Fe^{3+} \rightarrow Fe_4[Fe(CN)_6]_3$$

Also a strongly blue coloured complex can be formed by the reactants by the reaction:

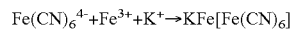
$$Fe(CN)_6^{4-} + Fe^{3+} + K^+ \rightarrow KFe[Fe(CN)_6]$$

Both the above reactions are substantially irreversible, and none of the mentioned reactants or the formed products are poisonous to human health and hence do not represent a hazard to consumers.

The material for immobilizing the reactant can e.g. be a gel based on a hydrocolloid, such as an alginate, a carrageenan, an agar, a pectin, a starch, a gum, a cellulose, a protein or other organic polymers having reacting functional groups. The concentration of the hydrocolloid in the gel is advantageously in the range of 0.1 to 20% such as in the range of 0.1 to 2% by weight. The gel can further comprise an alcohol such as glycerol. Prior to activation of the system the immobilized reactant is typically present at a concentration which is in the range of 0.01 to 1M, such as about 0.1 M. The immobilization of the reactant is typically performed by slowly adding a 0.1 M $FeCl_3$ solution to a mixture comprising alginate, glycerol and water, while stirring vigorously. However, it is also within the scope of the invention to use a particulate polymeric matter such as a resin as material for immobilization, e.g. a cation or anion exchange resin.

Prior to activation of the time-temperature indicator system, the mobile reactant is present in the system at a concentration which is in the range of 0.01 to 1M, such as about 0.1 M, in a mixture comprising alginate, glycerol and water.

The time-temperature indicator system according to the invention can advantageously be a system wherein the reactants are contained in a cylinder element consisting of two compartments separated by a sealing. Such a cylinder element can be made of different materials such as glass and polymeric materials. Such a polymeric material can e.g. be polyethylene. The sealing between the two compartments may be provided by bending the cylinder element to occlude the transition between the compartments or it may be provided by a barrier such as thin polymer film. The barrier may also be provided by means of a material such as e.g. a wax, which is solid within a certain temperature range, but flows when a given threshold temperature is exceeded.

The system is typically activated by breaking or removing the sealing between the two compartments containing the reactants. The breaking can e.g. be performed by means of exposing the sealing to mechanical stress, irradiation or heat.

However, it is also contemplated that the reactants can be contained in a disc shaped carrier element comprising a central portion containing one reactant and a peripheral portion containing the other reactant. The disc shaped carrier element can be made of e.g. a polymer wherein a part of the carrier element is a gel wherein one reactant is immobilized. Additionally, also a system wherein the reactants are contained in a rectangular strip shaped element is within the scope of the invention. Such a strip shaped element is conveniently made of a cellulosic or a polymeric material.

The system according to the invention is capable of indicating the time-temperature history within a temperature range having a difference between the upper and lower limit which is at the most 50° C. preferably in the temperature range of −20° C. to 30° C. such as in the range of −20° C. to 4° C. However the system according to the invention is also capable of indicating the time-temperature history in the temperature range of 30° C. to 90° C.

In a further aspect of the invention, there is provided a method for monitoring the time-temperature history of a product, comprising defining a typical (i.e., a reference or a standard) time-temperature history for the product which results in a desired or an undesired change of the product, constructing a system according to the invention which, when subjected to such a typical time-temperature history, provides a visually detectable reaction signal which indicates that the desired or the undesired change of the product is imminent, associating the product with the thus constructed system, activating the system and following the visually detectable reaction signal during storage of the product.

Such products include e.g. food products, chemical products, pharmaceutical products, cosmetics or biological materials. Typically such food products are products which are fresh, frozen, preserved or dehydrated, and typical biological materials are products like e.g. diagnostic reagents, plants, seeds and semen.

It is also within the scope of the invention that the above system can be associated with a container for the products described above. Typical containers are e.g. cans, trays, bags and jars. The association of the system to such containers can be provided by means of an adhesive layer on the system by which the system will be substantially irremovable when associated with the container. The association of the system to the container can be constructed in such a way that if the system is attempted to be removed from the container by which it is associated, it will break or be destroyed. By this it can be prevented that the system is abused.

In yet a further aspect of the invention, there is provided a method for producing a system according to the invention, comprising selecting at least two reactants which, when brought into contact, provides a visually detectable chemical reaction, immobilizing one of the reactants in a medium which permits the other of the reactants to become mobile, enclosing the mobile reactant and the medium containing the immobilized reactant in adjacent compartments separated by a breakable sealing.

There is also provided a container associated with a system according to the invention, wherein the system is associated with an inner or outer surface of the container or wherein the system is integrated in the container material. The system can e.g. be associated with the inner surface of a polymer film used for the wrapping of fresh meat, or the system can e.g. be integrated in a container for food such as a tray for meat packaging or a milk container.

FIGS. 1-4 illustrate some of the conceptual, exemplary, non-limiting embodiments of the invention. These figures are not intended to imply any particular dimensions of the elements of the illustrated embodiments, or relative proportions between parts (components) of elements of the illustrated embodiments. Rather, the figures, as stated above, are a representation of the concepts embodied via exemplary embodiments of our system.

Figure 2:
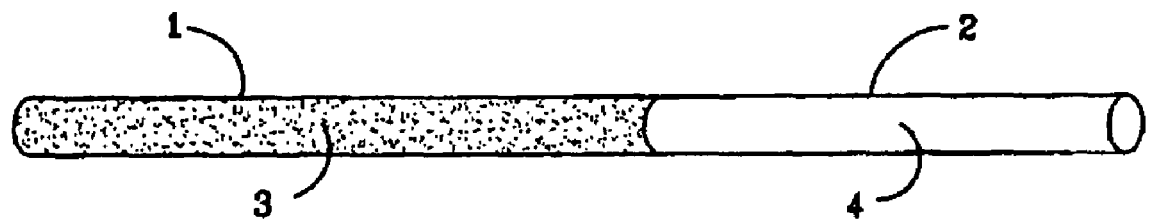
FIG. 2 is a conceptual representation of the embodiment of FIG. 1 after activation.

FIG. 1 illustrates a conceptual embodiment of the invention wherein the reactants are contained in a cylinder element including two compartments, and a sealing (or a seal) between the two compartments which is provided by bending the cylinder element. Thus, compartment 1 includes an immobile reactant 3 and compartment 2 includes a mobile reactant 4. The seal between the two compartments occludes transition between the compartments. In FIG. 2, the seal is removed by unbending the cylinder element.

Figure 3:
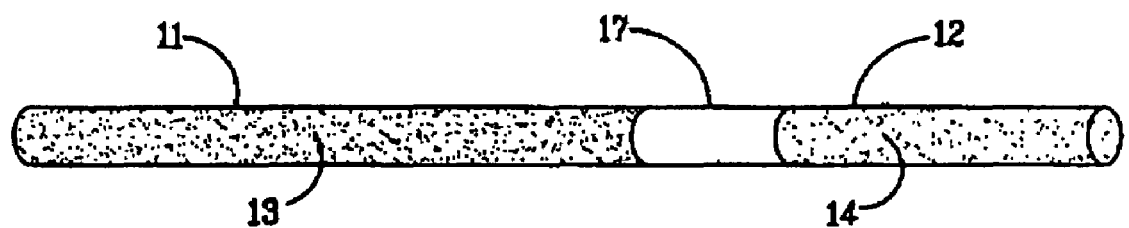
FIG. 3 is a conceptual representation of another exemplary embodiment of the system of the invention.

In FIG. 3, the reactants are contained in a cylinder element and the sealing between the two compartments is provided by a barrier 17, made of a material different from the immobilized and mobile reactants, such as wax. In this conceptual embodiment, compartment 11 includes an immobile reactant 13, and compartment 12 includes a mobile reactant 14.

Figure 4:
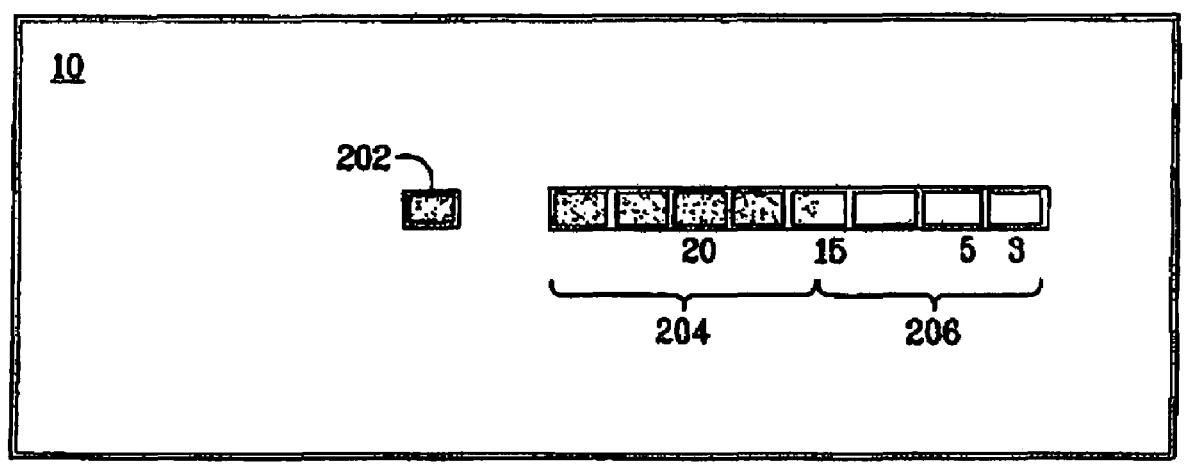
FIG. 4 is a conceptual representation of yet another exemplary embodiment of the invention.

FIG. 4 illustrates a conceptual embodiment, which is a rectangular strip-shaped element 10. In this embodiment, a component 202 indicates whether the element 10 is or is not activated. Component 204 indicates the time-temperature integral elapsed, e.g., the number of days at a given temperature that the strip-shaped element experienced. Component 206 indicates the remaining time-temperature integral, e.g., the number of days at a given temperature remaining until the desired or undesired change occurs.

The invention will now be described by way of illustration in the following non-limiting examples.

EXAMPLE 1

Preparation of the Mobile and the Immbolized Reactant

The mobile reactant is a 0.1M solution of $K_4Fe(CN)_6$ in a mixture of 0.64% (w/w) alginate, 47.29% (w/w) glycerol, 52.06% (w/w) water.

The immobilized reactant is prepared by slowly adding a 0.1 M $FeCl_3$ solution in a mixture of 47% (w/w) glycerol and 53% (w/w) water to a mixture of 0.64% (w/w) alginate, 47.29% glycerol and 52.06% (w/w) water. The amount of 0.1 M $FeCl_3$ solution is 17% (w/w) of final weight. The mixing is done at room temperature by stirring vigorously. By this method a viscous liquid is achieved wherein small gel lumps containing immobilized $Fe^{3+}$ are equally dispersed.

EXAMPLE 2

Time-temperature Indicator Prepared as an Ampoule

For preparing a time-temperature indicator as an ampoule, two transparent cylinders made of polystyrene, each of them closed in one or the ends were applied. One of the cylinders (No. 1) was able to fit into the other cylinder (No. 2) by having an outer diameter which was equal to the inner diameter of cylinder No. 2.

The mobile reactant was prepared as described in Example 1 and contained $K_4Fe(CN)_6$ at a concentration of 0.1 M. The mobile reactant was transferred to cylinder No. 1.

The immobilized reactant containing $Fe^{3+}$ ions immobilized in the alginate gel was prepared as described in Example 1 and subsequently transferred to cylinder No. 2.

The two cylinders were assembled by gently pressing them together, carefully avoiding formation of air bubbles in the cylinders, and by this the chemical reaction was started.

The time-temperature indicator was incubated and regularly inspected for coloration of the gel. The mobile reactant, the $Fe(CN)_6^{4-}$-ions, diffused from the liquid into the gel where it reacted with the $Fe^{3+}$-ions immobilized therein which was visualised by the gel becoming strongly blue coloured. The extent of the coloration was an indication of the exposure to both time and temperature, corresponding to a 1. order reaction.

EXAMPLE 3

Colour Development as Function of Time at 4° C. in a Strip Shaped Time-temperature Indicator A time-temperature indicator was prepared as a strip wherein the reactants were prepared as described in the above example 1.

The colour development in the part of the strip-shaped time-temperature indicator containing the immobilized $Fe^{3+}$ was monitored. The colour development was measured in percentages as the length of the strongly blue coloured zone compared to the total length of the part of the time-temperature indicator containing the immobilized reactant. The time-temperature indicator was kept at a constant temperature of 4° C. for 76 days.

The results of the above experiment is presented in the below Table 3.1.

TABLE 3.1

| Days | Colour development (%) |
|---|---|
| 0 | 0 |
| 19 | 50 |
| 38 | 75 |
| 57 | 88 |
| 76 | 93 |

It is apparent from the above results that the time-temperature indicator responds well to the exposure of time at a constant temperature.

EXAMPLE 4

Colour Development as Function of Time at 4° C. and −20° C.

Two identical time-temperature indicators were prepared as described in the above example 3, and the colour development was measured at 4° C. and −20° C., respectively.

The results of this experiment is presented in Table 4.1.

TABLE 4.1

| Days | Colour development +4° C. (%) | Colour development −20° C. (%) |
|---|---|---|
| 0 | 0 | 0 |
| 10.9 | 50 | 8 |
| 21.8 | 74 | 15 |
| 32.7 | 86 | 22 |
| 43.6 | 92 | 28 |

As can be seen from the above results, the colour development is not only time dependent but also temperature dependent. After 43.6 days 92% of the strip held at 4° C. was blue coloured, whereas only 28% of the strip held at −20° C. was blue coloured.

There was an inverse correlation between the diffusion rate of the mobile reactant and the ambient temperature. The lower the temperature, the slower the mobile reactant was moving and hence the slower the time-temperature indicator was blue coloured. This enhances the reproducibility and hence the predictability of the response.

The invention claimed is:

1. A full-history time-temperature indicator system which exhibits a time-temperature dependent and visually detectable, substantially irreversible chemical reaction, which system responds independently of a temperature threshold and provides a cumulative response to the time and storage conditions to which the system has been exposed, the system comprising at least one immobilized and at least one mobile reactant, at least one of said immobilized and mobile reactants comprising a metal compound, said immobilized reactant being immobilized in a hydrocolloid gel contained in a first compartment adjacent to a separate second compartment containing the mobile reactant, and said at least one immobilized and at least one mobile reactant initially being separated by a seal to prevent contact between the reactants, the system being activated by removing the seal between the compartments, to allow for the mobile reactant to diffuse through the hydrocolloid gel, wherein the diffusion rate is temperature dependent, and to move through the immobilized reactant, which remains immobilized in the hydrocolloid gel, in a time-temperature dependent manner resulting in a visually detectable and substantially irreversible signal that can be followed from the time of activation and said irreversible signal indicating a full, continuously cumulative time-temperature history.

2. A system according to claim 1, wherein the metal compound is of a metal from the transition metal Groups IB-VIIIB, a metal compound of a metal from the Groups IIIA, IVA or VA or a metal compound of an element from the rare-earth elements Group of the Periodic Table of Elements (Lanthanoids).

3. A system according to claim 2, wherein the metal compound is an ion selected from the group consisting of Fe, Al and Mn.

4. A system according to claim 1, wherein the mobile reactant is $Fe(CN)_6^{4-}$.

5. A system according to claim 1, wherein the mobile reactant is $Fe^{3+}$.

6. A system according to claim 1, wherein the chemical reaction between the reactants is a redox process and/or is selected from the group consisting of a complex formation, a chelate formation and a precipitation.

7. A system according to claim 6, wherein the complex is formed by at least one of the following chemical reactions:

$$3Fe(CN)_6^{4-} + 4Fe^{3+} \rightarrow Fe_4[Fe(CN)_6]_3$$

$$Fe(CN)_6^{4-} + Fe^{3+} + K^+ \rightarrow KFe[Fe(CN)_6]_2.$$

8. A system according to claim 1, wherein the chemical reaction is visually detectable by a change in color.

9. A system according to claim 1, wherein the hydrocolloid is selected from the group consisting of an alginate, a carrageenan, an agar, a pectin, a starch, a gum, a cellulose and a protein.

10. A system according to claim 1, wherein the concentration of the hydrocolloid in the gel is in the range of 0.1 to 20% by weight.

11. A system according to claim 1, wherein the gel comprises an alcohol.

12. A system according to claim 11, wherein the alcohol is glycerol.

13. A system according to claim 1, wherein the immobilized reactant prior to activation of the system is present at a concentration which is in the range of 0.01 to 1M.

14. A system according to claim 1, wherein the mobile reactant prior to activation of the system is present at a concentration which is in the range of 0.01 to 1M.

15. A system according to claim 1, wherein the reactants are contained in a cylinder element consisting of two compartments separated by said seal.

16. A system according to claim 15, wherein the cylinder element is made of a material selected from the group consisting of a glass and a polymeric material.

17. A system according to claim 1, where the reactants are contained in a disc shaped carrier element comprising a central portion containing one reactant and a peripheral portion containing the other reactant.

18. A system according to claim 17, where at least part of the carrier element is said hydrocolloid gel wherein one reactant is immobilized.

19. A system according to claim 1, where the reactants are contained in a strip shaped element.

20. A system according to claim 1, wherein the system indicates the time-temperature history within a temperature range having a difference between the upper and lower limit which is at most 50° C.

21. A system according to claim 20, wherein the system indicates the time-temperature history in a temperature range of −20° C. to 30° C.

22. A system according to claim 21, where the temperature range is −20° C. to 4° C.

23. A system according to claim 21, where the temperature range is 30° C. to 90° C.

24. A method for monitoring the time-temperature history of a product, comprising defining a typical time-temperature history for said product which results in a desired or an undesired change of the product, constructing a system according to claim 1 which, when subjected to such a typical time-temperature history, provides a visually detectable and substantially irreversible reaction signal which indicates that the desired or the undesired change of the product is imminent, associating the product with the thus constructed system, activating the system and following the visually detectable reaction signal during storage of the product.

25. A method according to claim 24, wherein the product is selected from the group consisting of a food product, a chemical product, a pharmaceutical product, cosmetic and a biological material.

26. A method according to claim 25, wherein the product is a food product selected from the group consisting of fresh, frozen, preserved and dehydrated food product.

27. A method according to claim 24, wherein the system is attachable to a container for the product.

28. A method for producing a system as defined in claim 1, comprising selecting at least two reactants which, when brought into contact, provide a visually detectable and substantially irreversible chemical reaction, immobilizing one of said reactants in a medium, enclosing the mobile reactant and the medium containing the immobilized reactant in adjacent compartments separated by a removable seal.

29. A combination of the system of claim 1 with a perishable product storage container.

30. The combination of claim 29, wherein the system is attached to an inner or outer surface of the container.

31. The combination of claim 29, wherein the system is integrated in a container material of the container.

32. A system according to claim 13, wherein the immobilized reactant prior to activation of the system is present at a concentration about 0.1M.

33. A system according to claim 14, wherein the immobilized reactant prior to activation of the system is present at a concentration about 0.1M.

34. The system according to claim 1, wherein the rate of mobility of the mobile reactant is time-temperature dependent.

35. A system according to claim 1 wherein the immobilized reactant, the mobilized reactant and a product of a reaction between the immobilized reactant and the mobilized reactant are not poisonous to human health.

36. A system according to claim 1, wherein the concentration of the hydrocolloid in the gel is in the range of 0.1 to 2% by weight.

37. A full-history time-temperature indicator system which exhibits a time-temperature dependent and visually detectable, substantially irreversible chemical reaction, which system responds independently of a temperature threshold and provides a cumulative response to the time and storage conditions to which the system has been exposed, the system comprising a cylinder element including a first compartment adjacent to a second compartment, wherein the system further comprises at least one immobilized reactant immobilized in a hydrocolloid gel contained in the first compartment and at least one mobile reactant contained in the second compartment, at least one of said immobilized and mobile reactants comprising a metal compound, wherein the two compartments are separated by a seal to prevent contact between the reactants, wherein the seal is formed by bending the cylinder element to occlude transition between the compartments or the seal is comprised of a material distinct from the immobilized reactant and the mobile reactant, and the removal of the seal comprises unbending the cylinder element or breaking the seal, wherein the breaking includes mechanical stress, irradiation or heat the system being activated by removing the seal between the compartments to allow for the mobile reactant to diffuse through the hydrocolloid gel, wherein the diffusion rate is temperature dependent, and to move through the immobilized reactant, which remains immobilized, in the hydrocolloid gel, in a time-temperature dependent manner resulting in a visually detectable and substantially irreversible signal that can be followed from the time of activation and said substantially irreversible signal indicating a full, continuously cumulative time-temperature history.

38. The system according to claim 37, wherein the rate of mobility of the mobile reactant is time-temperature dependent.

* * * * *